United States Patent [19]

Chamness et al.

[11] 3,955,578

[45] May 11, 1976

[54] ROTATABLE SURGICAL SNARE

[75] Inventors: Dale L. Chamness; Thomas A. Osborne, both of Bloomington, Ind.

[73] Assignee: Cook Inc., Bloomington, Ind.

[22] Filed: Dec. 23, 1974

[21] Appl. No.: 535,420

[52] U.S. Cl. .......................... 128/303.15; 128/320
[51] Int. Cl.² .................. A61B 17/32; A61N 3/00
[58] Field of Search ............... 128/303.15, 303.14, 128/303.16, 303.17, 307, 309, 320; 30/116

[56] References Cited
UNITED STATES PATENTS

| | | | |
|---|---|---|---|
| 1,731,069 | 10/1929 | Herman | 128/303.16 |
| 1,971,024 | 8/1934 | Wappler | 128/303.17 |
| 2,448,741 | 9/1948 | Scott et al. | 128/303.15 |
| 2,484,059 | 10/1949 | Wallace | 128/303.15 |
| 2,888,017 | 5/1959 | Wallace | 128/303.15 |
| 3,532,095 | 10/1970 | Miller | 128/303.17 |
| 3,805,791 | 4/1974 | Sevberth et al. | 128/303.14 |
| 3,828,790 | 8/1974 | Curtiss | 128/303.14 |

*Primary Examiner*—Robert W. Michell
*Assistant Examiner*—Lee S. Cohen
*Attorney, Agent, or Firm*—Woodard, Weikart, Emhardt & Naughton

[57] ABSTRACT

A rotatable endoscopic surgical snare having an operating loop which is rotatable about the longitudinal axis of a torque transmitting center member connecting the operating loop to an electrical power supply. The operating loop is retractable and protractable into and from a protective flexible sheath. The operating loop is formed of a resilient spiral sleeve through which a core member extends.

11 Claims, 8 Drawing Figures

ROTATABLE SURGICAL SNARE

BACKGROUND OF THE INVENTION

1. Field of the Invention

This invention relates to a surgical instrument and, more particularly, to a surgical snare suitable for use in carrying out polypectomy procedures.

2. Description of the Prior Art

Surgical snares suitable for use in removing polyps, such as those which are found in the colon of surgical patients, have been in use for many years. Although such instruments have been used with some success, they have left a great deal to be desired. Surgical snares in general have comprised an elongated flexible sheath connected at its proximal end to an operating handle. Extending through the sheath is an elongated flexible cable, the proximal end portion of which is connected to a movable portion of the operating handle so that the cable can be retracted and protracted by the surgeon relative to the sheath. An operating loop is connected to the distal end portion of the cable which is opened and closed by the surgeon to the extent that he shifts the movable portion of the operating handle to protract or retract the cable. When the cable is in its protracted or forward position, the operating loop is outside the sheath and in its fully extended position. As the cable is retracted, the loop is drawn into the sheath and closed.

Previous surgical snares have generally suffered from common deficiencies such as ease of manipulation of the operating loop at the point of application, usually within the gastrointestinal tract of a surgical patient. As can be appreciated, during periods of actual use, a surgical snare must be manipulated and operated with a high degree of precision and control. Additionally, due to the fact that a cauterizing and cutting electrical current is generally used, the surgical loop cannot touch portions of the body other than the one which is to be removed. In light of this, prior manufacturers have attempted to use a very thin wire as the operating loop. While the thin wire allows more convenient manipulation, it also presents a serious and potentially lethal problem in that frequently there is premature severing of the polyp. This can lead to internal bleeding and infection, neither of which is acceptable in modern surgical procedures. As a result of this, the operating loop was made using a resilient spiral sleeve through which a core member was extended. Thus, the width was great enough to effectively prevent unnecessary, premature removal of the polyp during strangulation and at the same time was small enough to allow a tolerable degree of manipulation. This recent development is shown and described in U.S. Pat. No. 3,828,790 (1974) to Curtiss et al which is relevant prior art.

In addition, existing snare handles for use with the available surgical snares are manufactured in a manner such that in order to rotate the operating loop, while trying to engage the polyp, it is necessary to rotate the entire handle in order to rotate the operating loop. The operating loop handle usually has an electrical wire connected to an RF generator. While rotating the entire handle, the wire has a tendency to become wrapped around the surgeon's hand and is in general an unwieldy method for rotating the snare. In light of this, a need has arisen for a surgical snare having an operating loop which is freely rotatable while the handle remains relatively stationary.

Other relevant prior art is Wallace, U.S. Pat. Nos. 2,484,059 (1949), 2,545,865 (1951) and 2,888,017 (1959); Scott et al, U.S. Pat. No. 2,448,741 (1948); Willinsky, U.S. Pat. No. 2,487,502 (1949); Zingale, U.S. Pat. No. 3,149,633 (1964); Wappler, U.S. Pat. No. 3,752,159 (1973); and Seuberth Pat. al, U.S. Patent No. 3,805,791 (1974).

SUMMARY OF THE INVENTION

This invention relates to a surgical snare comprising the combination of an elongated flexible sheath and a torque transmitting center member which extends through and is rotatable in the sheath. An electrically conductive snare loop means is connected to the distal end portion of the center member with actuating means connected to the proximal end portion of the center member. The actuating means permits moving the center member relative to the sheath between the retracted position in which the snare loop means is nested within the sheath and an extended position in which the snare loop means extends beyond the distal end of the sheath and is free to open and form a loop. Rotating means are rotatably mounted on the actuating means for rotating the center member about its longitudinal axis. Means are provided for electrically connecting the snare loop means to a power source.

It is an object of this invention to provide a surgical snare controlled by a stationary, remote handle portion which has an operating loop which is electrically conductive, flexible and rotatable.

It is a further object of this invention to provide a surgical snare having means for retracting and extending an operating loop from a protective sheath.

It is a still further object of this invention to provide a surgical snare whereby a rotatable operating loop is connected to a source of electrical energy.

These and other objects of this invention will become apparent from the following description of the preferred embodiment.

DESCRIPTIION OF THE DRAWING

Figure 1:
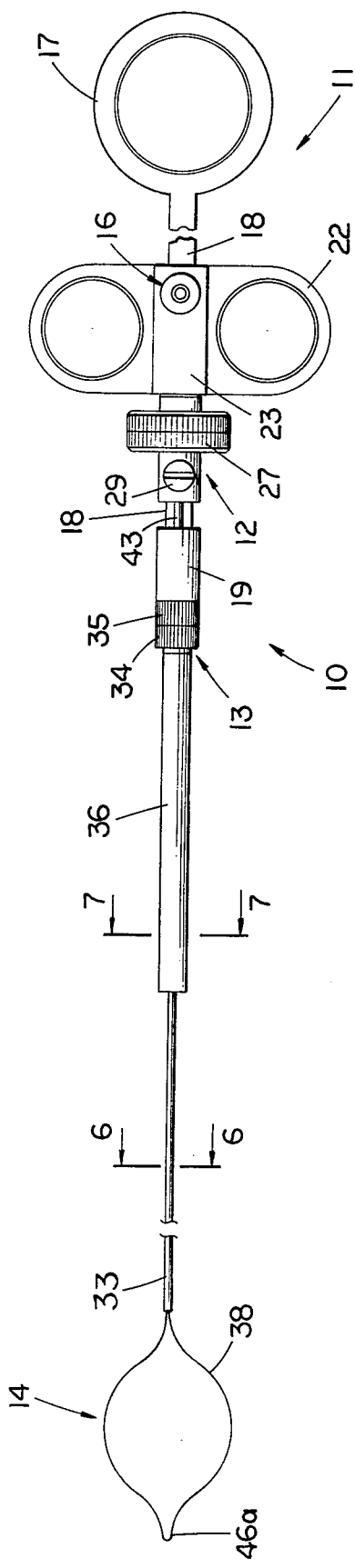
FIG. 1 is a top view of a surgical snare constructed in accordance with the present invention and showing the operating loop in its protracted position.
Figure 2:
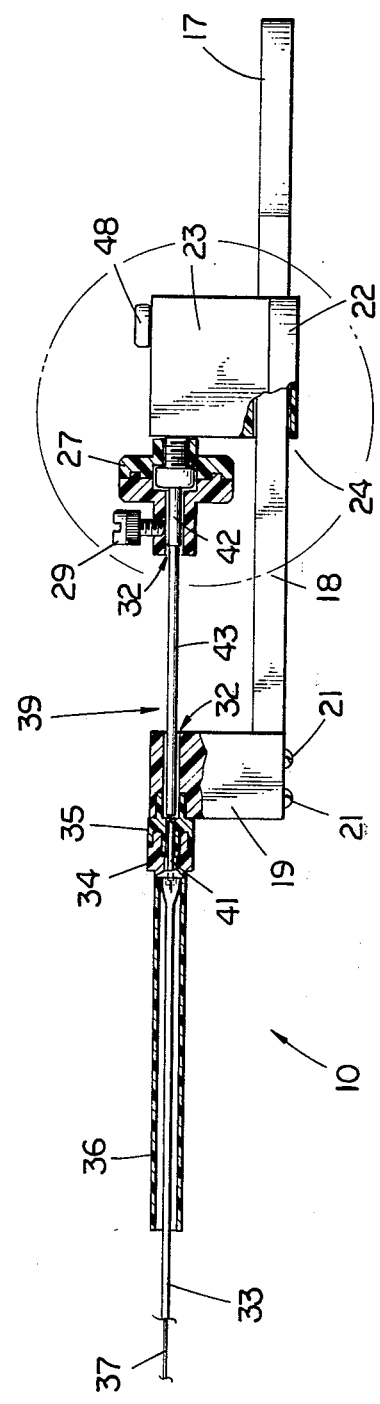
FIG. 2 is a plan view, partially in section, of a surgical snare constructed in accordance with the present invention.
Figure 3:
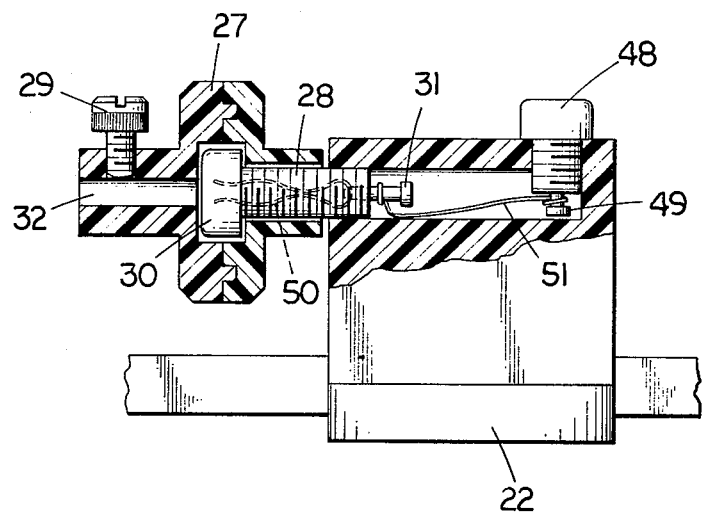
FIG. 3 is an enlarged plan view in cross section of the area circled in FIG. 2.
Figure 6:
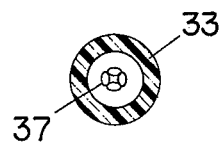
Figure 8:
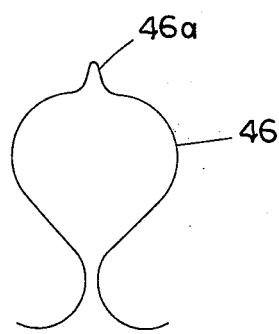
Figure 7:
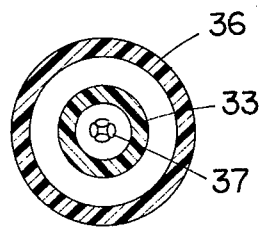

FIGS. 6 and 7 are enlarged cross-sectional views taken respectively along the lines 6—6 and 7—7 of FIG. 1;

FIG. 8 is a plan view of the operating loop core member.

DESCRIPTION OF THE PREFERRED EMBODIMENT

For the purposes of promoting an understanding of the principles of the invention, reference will now be made to the embodiment illustrated in the drawing and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawing, the rotatable surgical snare 10 comprises a finger grip assembly 11, a rotating assembly 12, a sheath assembly 13, an operating loop assembly 14 and an electrical assembly 16. The finger grip assembly 11 comprises a thumb grip 17 integrally attached to the proximal end of a stem 18. Preferably the thumb grip 17 and stem 18 are molded as a single piece. At the distal end of stem 18 is a retainer block 19. Retainer block 19 is fixedly held in place by screws 21.

Finger grips 22 are integrally attached to movable member 23 and preferably finger grips 22 and movable member 23 are molded as a single piece. Movable member 23 is linearly moveable on stem 18 from a position adjacent thumb grip 17 to a position adjacent retainer block 19. Stem 18 extends through an opening 24 in movable member 23 to allow linear movement of member 23. When retainer block 19 is attached to stem 18 by screws 21 movable member 23 is restricted in movement between the thumb grip 17 and the retainer block 19. Both the stem 18 and the opening 24 have a square cross-sectional area to prevent rotational movement of member 23.

Attached to sliding member 23 is rotating assembly 12. Rotating assembly 12 comprises a handle 27, a threaded jack 28, and set screw 29. Threaded jack 28 is threadedly fixed to movable member 23. Handle 27 is rotatably mounted on threaded jack 28. The head 30 of jack 28 prevents handle 27 from being disengaged from movable member 23. Set screw 29 is threadedly received by handle 27. Linear bores 32 extend through retainer block 19 and handle 27 and into threaded jack 28. Linear bores 32 allow connection of the operating loop assembly 14 to the electrical power source. A soldering terminal 31 is attached to the proximal end of threaded jack 28.

The sheath assembly 13 comprises an elongated flexible sheath 33, the proximal end of which is engaged by threaded retaining member 34. Threaded retaining member 34 is threadedly attached to a threaded connecting member 35 which in turn is threadedly attached to retainer block 19. An elongated flexible tube 36 extends a portion of the length of sheath 33 and is fittingly engaged by the sheath 33 at the junction of sheath 33 and retaining member 34. The sheath assembly 13 including the sheath 33, retaining member 34, connecting member 35, and tube 36 are made using electrically non-conductive material. The length of elongated flexible sheath 33 may vary, as desired, to conform with the intended use of the surgical snare 10 and is just enough shorter than the operating loop assembly 14 so that the latter, in its protracted position, is positioned with its loop extending outside the distal end of sheath 33.

The operating loop assembly 14 comprises a torque transmitting center member 37 having an operating loop 38 attached to its distal end. The distal end of a wire lead 39 is attached to the proximal end of center member 37. The point of attachment between lead 39 and center member 37 is surrounded by a protective sleeve 41. Wire lead 39 is substantially more rigid than torque transmitting center member 37. A conductive sleeve 42 is attached to the proximal end of lead 39 to form the point of electrical contact between the operating loop assembly 14 and electrical assembly 16. Substantially the entire length of lead 39 between sleeves 41 and 42 is covered by a protective coating 43 of electrically non-conductive plastic or rubber material. The center member 37, operating loop 38, wire lead 39, and sleeves 41 and 42 are all made using electrically conductive materials.

Figure 4:
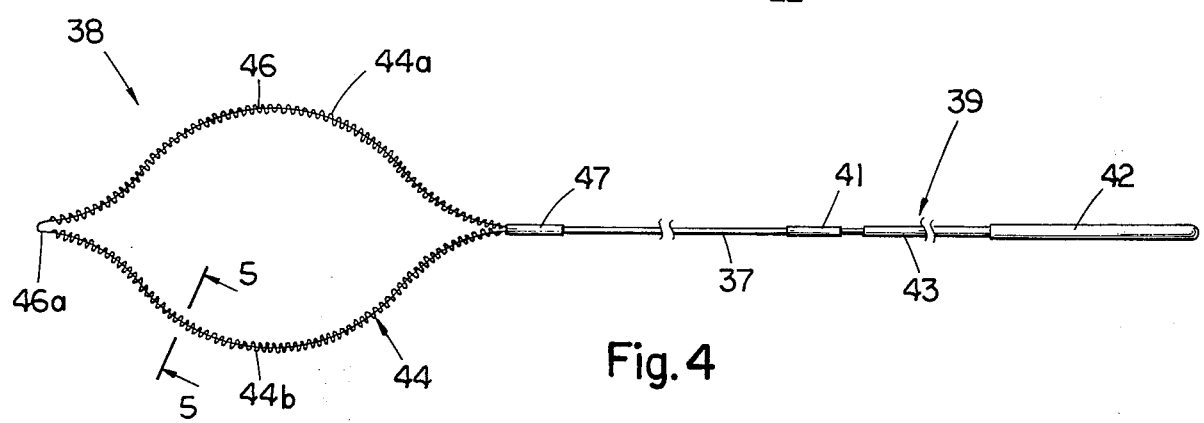
FIG. 4 is a plan view of the operating loop assembly removed from the finger grip assembly.
Figure 5:
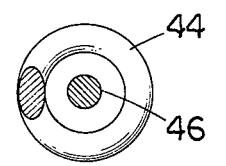
FIG. 5 is an enlarged cross-sectional view of the operating loop assembly taken along the line 5—5 of FIG. 4.

Operating loop 38 comprises a spiral sleeve 44 through which extends a flat or round resilient core 46 forming a spring which when unconfined preferably has the shape shown in FIG. 8 and normally urges the operating loop 38 to the shapes shown in FIGS. 1 and 4. As shown, spiral sleeve 44 comprises two spiral members 44a and 44b having their distal ends spaced to facilitate the flexing of the core 46 at its cusp 46a when the operating loop 38 is drawn into or extended from the sheath 33. The proximal ends of the sleeve 44 and the proximal ends of core 46 are soldered together and to the distal end of center member 37. The point of attachment between sleeve 44, core 46 and center member 37 is surrounded by a protective sleeve 47. Spiral members 44a and 44b and core 46 are advantageously formed from austenitic stainless steel. While the dimensions of the sleeve 44 and core 46 may vary, the core should be thick enough to provide the required strength. The spiral members 44a and 44b are wound relatively loosely from stainless steel wire with the space between adjacent turns of the helix equal to from about one-sixth to about twice, preferably about one-third, the diameter of the helix wire. The spiral sleeve 44 is made from wire having a diameter of about 0.006 inches wound to an outer diameter of about 0.023 inches with spacing between adjacent turns of the helix equal to about 0.002 inches.

The electrical assembly 16 comprises a threaded jack 48, a soldering terminal 49, a leaf spring 50, and a connecting wire 51. Threaded jack 48 is threadedly received by movable member 23. A leaf spring 50 is mounted within the bore 32 in jack 28 such that sleeve 42 engages leaf spring 50 when the operating loop assembly 14 is properly positioned. Electrical contact between leaf spring 50 and sleeve 42 is maintained during rotation of operating loop assembly 14. Threaded jack 48 and threaded jack 28 are electrically connected by connector wire 51 which extends between and is soldered to soldering terminals 31 and 49.

Thus, during assembly, the wire lead 39 is threaded through linear bores 32 such that the conductive sleeve 42 extends into linear bore 32 of the jack 28 and such that it makes contact with leaf spring 50. The surgical snare 10 is inserted and operated within a patient using well-known techniques which form no part of the present invention and, thus, need not be discussed further here. However, it should be noted that surgical snare 10 constructed and assembled in accordance with the present invention provides a surgical snare which is not only sized appropriately to be conveniently handled and manipulated, but also can be rotated without requiring simultaneous rotation of the finger grip assembly 11. The operating loop assembly 14 is readily disengaged by unscrewing set screw 29 and can be completely withdrawn for straightening or replacement and then reinserted without disturbing the position of the finger grip assembly 11 and the sheath 33 or the patient. The structure of the operating loop 38 not only minimizes the likelihood of deformation in use, but also, the core facilitates reshaping if that should be necessary.

The center member 37 and especially the conductive sleeve 42 is held in place during use by turning set screw 29 until it compresses center member 37 and holds it tightly.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A surgical snare comprising the combination of:
   a. an elongated flexibly bendable sheath having proximal and distal ends;
   b. a torque transmitting electrically conductive center member extending in said sheath having proximal and distal ends adjacent those of the sheath and being rotatable therein, said center member also being flexibly bendable with said sheath to conform to tortuous body cavities;
   c. an electrically conductive snare loop means connected to the distal end portion of said center member, said center member and said snare loop means each forming a part of an operating loop assembly which is the only structure in said sheath;
   d. actuating means connected to the proximal end portion of said center member and to said sheath for moving said center member relative to said sheath between a retracted position in which said snare loop means is nested within said sheath and an extended position in which said snare loop means extends beyond the distal end of said sheath and is free to open and form a loop;
   e. rotating means rotatably mounted on said actuating means for rotating said center member about its longitudinal axis while said actuating means remains stationary; and
   f. means for electrically connecting said snare loop means to a power source through said center member.

2. The surgical snare combination of claim 1 wherein said means for electrically connecting said snare loop means to a power source comprises an electrically conductive leaf spring mounted on said actuating means, an electrically conductive sleeve fixedly mounted on the proximal end of said center member in contact with said leaf spring, said leaf spring maintaining contact with said sleeve during rotation of said center member.

3. The surgical snare combination of claim 1 wherein said rotating means has a linear bore therein and includes clamping means for fixedly retaining said center member in said linear bore.

4. The surgical snare combination of claim 3 wherein said rotating means includes a knurled cylindrical handle rotatably mounted on said actuating means and wherein said means for electrically connecting said snare loop means to a power source comprises an electrically conductive leaf spring mounted on said actuating means, an electrically conductive sleeve fixedly mounted on the proximal end of said center member in contact with said leaf spring, said leaf spring maintaining contact with said sleeve during rotation of said center member.

5. The surgical snare combination of claim 1 wherein the exposed surfaces of said sheath and center member proximal to said snare loop means are substantially covered with an electrically insulating material.

6. The surgical snare combination of claim 1 wherein said elongated flexible sheath is formed of an electrically insulating material.

7. The surgical snare combination of claim 6 wherein said actuating means comprises a stem member having proximal and distal ends and a movable member, said stem member including a retainer block mounted on the distal end thereof and a thumb grip mounted on the proximal end thereof, said retainer block being connected to said sheath, said movable member being movable along a portion of the length of said stem member, said movable member having said rotating means and a pair of finger grips mounted thereon, said rotating means being fixed to said center member and rotatable on said movable member.

8. The surgical snare combination of claim 7 wherein said snare loop means comprises a flexible spiral sleeve and an elongated resilient core member extending in said spiral sleeve.

9. The surgical snare combination of claim 1 wherein said means for electrically connecting said snare comprises an electrically conductive sleeve surrounding a portion of the length of the proximal end of said center member, said sleeve being removably received by said actuating means.

10. The surgical snare combination of claim 9 wherein a sleeve surrounds the connection of said snare loop means to the distal end of said center member.

11. The surgical snare combination of claim 10 wherein a tubular member surrounds a portion of said sheath, said tubular member being threadedly attached to said actuating means.

* * * * *